(12) United States Patent
Kakar et al.

(10) Patent No.: US 12,365,016 B2
(45) Date of Patent: *Jul. 22, 2025

(54) AUTOMATIC WASHER FOR CONTINUOUS POSITIVE AIRWAY PRESSURE EQUIPMENT

(71) Applicant: DR. KAKAR PRODUCTS, LLC, Plano, TX (US)

(72) Inventors: Rajdeep S. Kakar, McKinney, TX (US); Mohamed Abdelhares, Luxor (EG); Stewart Agustin, Nueva Vizcaya (PH)

(*) Notice: Subject to any disclaimer, the term of this patent is extended or adjusted under 35 U.S.C. 154(b) by 0 days.

This patent is subject to a terminal disclaimer.

(21) Appl. No.: 18/670,962

(22) Filed: May 22, 2024

(65) Prior Publication Data

US 2024/0307931 A1 Sep. 19, 2024

Related U.S. Application Data

(63) Continuation of application No. 17/076,455, filed on Oct. 21, 2020, now Pat. No. 12,030,096.

(Continued)

(51) Int. Cl.
| | |
|---|---|
| *B08B 9/032* | (2006.01) |
| *A61M 16/06* | (2006.01) |
| *A61M 16/08* | (2006.01) |
| *A61M 16/16* | (2006.01) |
| *B08B 9/023* | (2006.01) |

(52) U.S. Cl.
CPC ........... *B08B 9/0321* (2013.01); *A61M 16/06* (2013.01); *A61M 16/0875* (2013.01); *A61M 16/16* (2013.01); *B08B 9/023* (2013.01); *A61M 2209/10* (2013.01); *B08B 2209/032* (2013.01)

(58) Field of Classification Search
CPC ........... B08B 2209/00; B08B 2209/02; B08B 2209/027; B08B 2209/032; A47L 5/14; A47L 5/16; A47L 5/4278; A47L 15/508; A61L 2/18; A61L 2/183; A61L 2/186; A61M 2209/10; A61M 16/06;
(Continued)

(56) References Cited

U.S. PATENT DOCUMENTS

| | | |
|---|---|---|
| 3,101,728 A | 8/1963 | Broge |
| 5,184,635 A | 2/1993 | Tromblee et al. |

(Continued)

OTHER PUBLICATIONS

WO, International Search Report and Written Opinion, International Application No. PCT/US2020/059079 (Feb. 4, 2021) (9 pages).

*Primary Examiner* — David G Cormier
(74) *Attorney, Agent, or Firm* — FisherBroyles, LLP; Susan M. Oiler

(57) ABSTRACT

An automatic washer for continuous positive airway pressure equipment has a housing defining a wash chamber having an open face providing access to the wash chamber, a door selectively closing the open face, and a nozzle protruding into the wash chamber, a rack slidingly receivable within the wash chamber. The rack has a hose clamp oriented to secure an end of a CPAP hose when seated in the rack with an open end of the CPAP hose facing the nozzle. The nozzle has an air conduit that introduces air during a drying cycle and a water conduit that introduces water during a rinse cycle, and when the rack is fully inserted in the wash chamber, the nozzle is received inside the hose clamp, thereby, inside the CPAP hose when present.

20 Claims, 14 Drawing Sheets

Related U.S. Application Data

(60) Provisional application No. 62/933,212, filed on Nov. 8, 2019.

(58) Field of Classification Search
CPC ... A61M 16/0875; A61M 16/16; A61B 90/70; A61B 2090/701
See application file for complete search history.

(56) References Cited

U.S. PATENT DOCUMENTS

| | | |
|---|---|---|
| 5,275,668 A | 1/1994 | Dell et al. |
| 6,113,853 A | 9/2000 | Nakamura et al. |
| 8,276,603 B2 | 10/2012 | Berklund et al. |
| 8,821,807 B2 | 9/2014 | Schwartz et al. |
| 9,440,266 B2 | 9/2016 | Martineau et al. |
| 9,452,230 B2 | 9/2016 | Butrick |
| 9,623,452 B2 | 4/2017 | Przyjemski |
| 9,907,872 B2 | 3/2018 | Schmidt et al. |
| 2009/0266381 A1 | 10/2009 | Soderquist |
| 2011/0048464 A1 | 3/2011 | Rieger et al. |
| 2012/0145200 A1 | 6/2012 | Jerg et al. |
| 2013/0298945 A1 | 11/2013 | Yamamoto et al. |
| 2018/0020905 A1 | 1/2018 | Chouinard et al. |
| 2018/0318457 A1 | 11/2018 | Lucio |
| 2019/0167828 A1 | 6/2019 | Leyva |

AUTOMATIC WASHER FOR CONTINUOUS POSITIVE AIRWAY PRESSURE EQUIPMENT

RELATED APPLICATIONS

This application is a continuation of U.S. application Ser. No. 17/076,455, filed Oct. 21, 2020, which claims the benefit of U.S. Provisional Application No. 62/933,212, filed Nov. 8, 2019.

TECHNICAL FIELD

This application relates to automatic washers for continuous positive airway pressure (CPAP) equipment, more particularly, to a washer that automatically washes a CPAP hose, mask, and humidifier with a continuous flow of water either through direct connection to a water source, such as an under sink mounted machine or a portable machine, or via an on-board water reservoir.

BACKGROUND

CPAP equipment is a common treatment for obstructive sleep apnea. CPAP equipment utilizes a machine that is connected to a tight fitting mask worn by a user, the masking being connected to the machine by a hose to deliver continuous positive airway pressure. The problem is that there is no efficient and easy way to clean the hose, mask, and humidifier. Many users clean the hose, mask, and humidifier by hand, with an ozone treatment machine, or a UV light treatment machine.

Cleaning by hand is time consuming and inconvenient, and often results in a user cleaning the hose mask and humidifier less often than recommended. As such, there is an increased risk of infection and health problems, such as sinus infections, increased allergy symptoms, and facial irritation.

Ozone treatment machines use ionized air to clean the CPAP equipment. Ionized air can be harmful to the environment and there may be a risk of residual ozone being inhaled by users when not waiting the recommended length of time between cleaning and use of the CPAP equipment. There is a concern by some medical professionals that inhaling residual ozone may lead to chest pain, coughing, shortness of breath, and throat irritation. The U.S. Food and Drug Administration Code of Federal Regulations limits residual ozone to 0.05 parts per million.

UV light treatment machines have also been unsuccessful in cleaning CPAP equipment thoroughly and effectively. Some studies have shown that they are not completely effective in disinfecting CPAP equipment. With both UV light treatment machines and ozone treatment machines, a common problem is they do not remove dirt, grease, oils, and other residue from the CPAP equipment.

An automatic hose washing apparatus is disclosed in U.S. Pat. No. 9,623,452, but this machine recirculates used wash water over the hose and mask, which is undesirable. In particular, wash water passes through the interior of the hose before being sprayed over the exterior of the hose and mask, and only after this cycle is complete is the wash water drained from the device.

There is a need for an improved automatic CPAP equipment washer that overcomes the defects noted above, which effectively cleans the CPAP equipment with soap and water rather than ozone.

SUMMARY

In all aspects, an automatic washer for continuous positive airway pressure (CPAP) equipment is disclosed that has a housing defining a wash chamber having an open face providing access to the wash chamber, a door selectively closing the open face, a rack slidingly receivable within the wash chamber, a spray nozzle in the bottom surface of the wash chamber, and a dual eccentric nozzle protruding into the wash chamber. The rack has a hose clamp oriented to secure an end of a CPAP hose when seated in the rack with an open end of the CPAP hose facing the dual eccentric nozzle The dual eccentric nozzle has an air conduit that introduces air during a drying cycle and a water conduit that introduces water during a rinse cycle, and when the rack is fully inserted in the wash chamber, the dual eccentric nozzle is received inside the hose clamp, thereby, inside the CPAP hose when present. The washer has an on-off switch and a start-stop switch The spray nozzle can protrude into the wash chamber and can be a cone-shaped spray nozzle. In all embodiments, the spray nozzle has a 120 degree spray cone. A plurality of such spray nozzles can be present in the washer.

In all embodiments, a heated blower unit is present and is in fluid communication with the air conduit of the dual eccentric nozzle. The heated blower unit heats air to a maximum temperature of 110° F. (43.3° C.).

In all embodiments, the washer has a hot water inlet that is controlled by an electrically actuated valve and has a cold water inlet. The cold water inlet and the hot water inlet are in fluid communication with one another to mix the hot and cold water to form mixed water having a temperature within the range of 60° F. to 100° F. (15.6° C. to 37.8° C.). The mixed water is in fluid communication with a pressure restrictor to reduce the water pressure to be in a range of 5 psi to 50 psi (34.5 kPa to 344.7 kPa) at introduction to the wash chamber, thereby forming reduced pressure water. The reduced pressure water is in fluid communication with a mixing T coupler and the mixing T coupler is in fluid communication with a dosing pump for mixing cleaning solution with the reduced pressure water in the mixing T coupler, thereby forming wash water.

In all embodiments, a cleaning solution reservoir is in fluid communication with the dosing pump, and the mixing T coupler is in fluid communication with the spray nozzle and the water conduit of the dual eccentric nozzle to introduce wash water inside the CPAP hose and to the outside of the CPAP hose simultaneously.

In all embodiments, the rack has a plurality of hose routing features about interior sides of the rack and the rack is sized to hold a CPAP mask and CPAP humidifier water chamber interiorly relative to coils of the CPAP hose.

In all embodiments, a drain pump is in fluid communication with a drain in the bottom surface of the wash chamber can be present. The drain pump is active simultaneously with the introduction of water or wash water into the wash chamber.

DETAILED DESCRIPTION

Figure 1:
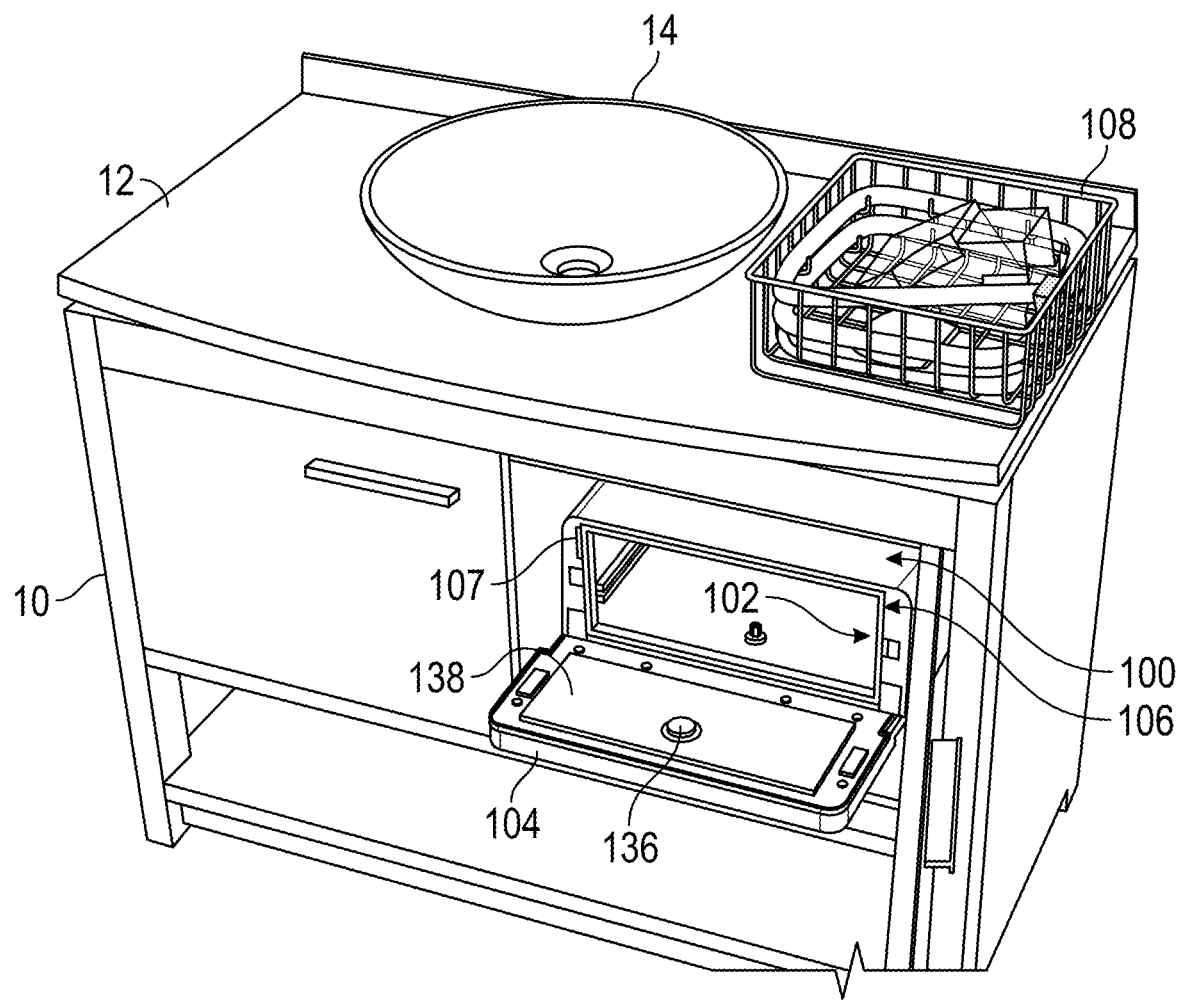
FIG. 1 is a perspective view of sink cabinet with an automatic CPAP washer mounted within the sink cabinet.

The following detailed description will illustrate the general principles of the invention, examples of which are additionally illustrated in the accompanying drawings. In the drawings, like reference numbers indicate identical or functionally similar elements.

FIG. 1 shows an undermount washer, generally designated by reference number 100, seated inside a sink vanity cabinet 10 having a countertop 10 and sink 14. The undermount washer 100 is illustrated as sitting on a shelf, but it could be mounted to an interior surface of the cabinet and/or the underside of the countertop 12 by brackets (not shown) mounted to the top portion of the undermount washer, thereby hanging the undermount washer within the cabinet. The undermount washer 100 defines a wash chamber 102, has door 104 that selectively opens and closes an open face 106 to provide access to the wash chamber 102. In one embodiment, the open face is a front face of the machine, thereby the rack 108 is slidingly receivable within the wash chamber 102. In another embodiment, the open face is a top face of the machine for a top-loading machine, especially when the machine pulls out of a cabinet on slides such as U.S. Pat. No. 4,739,781, or is a freestanding, portable countertop unit as in U.S. Pat. No. 5,518,014.

Figure 2:
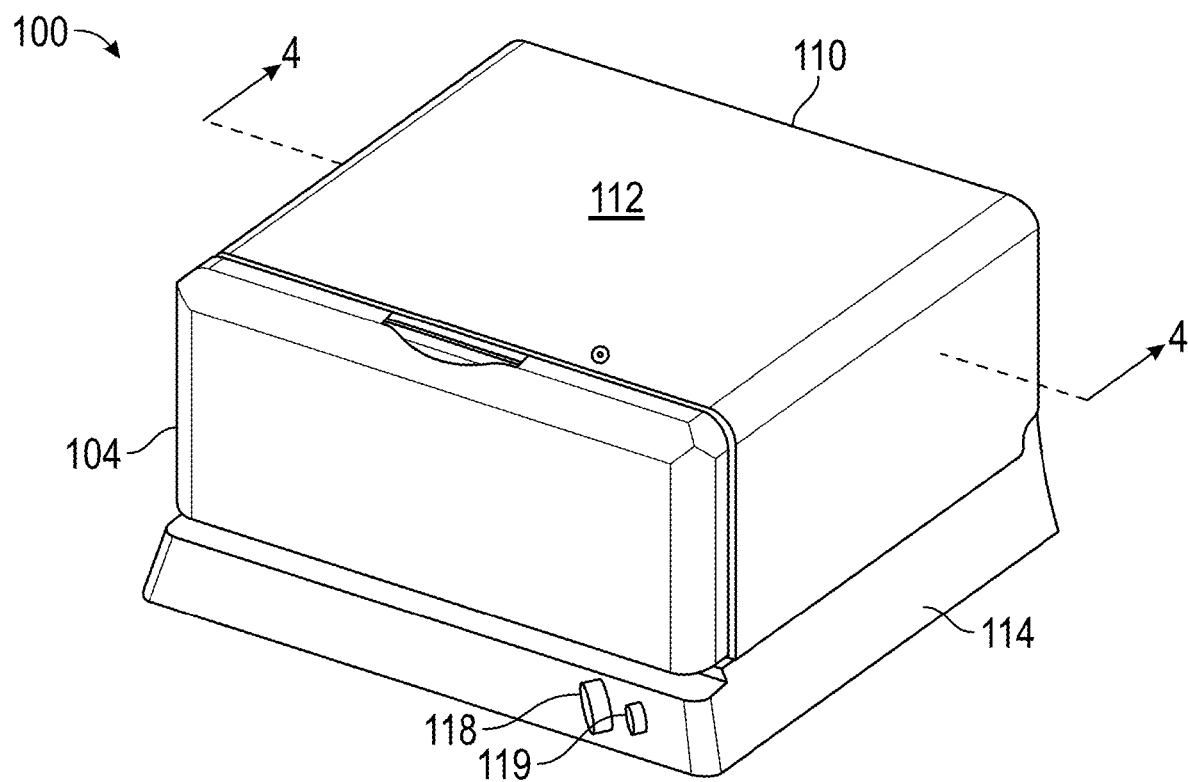
FIG. 2 is a front perspective view of an automatic CPAP washer.

Referring now to FIG. 2, the undermount washer 100 has a housing 110 that defines the wash chamber 102. The housing 110 includes the door 104, an outer shell 112, a skirt 114, and an inner shell 116 (best seen in the cross-section of FIG. 4). On the skirt 114 below the door 104 is an on-off switch 118 and a start-stop switch 119. Indicator lights may be present proximate the switches to indicate when the undermount washer 100 is in the on position.

Figure 3:
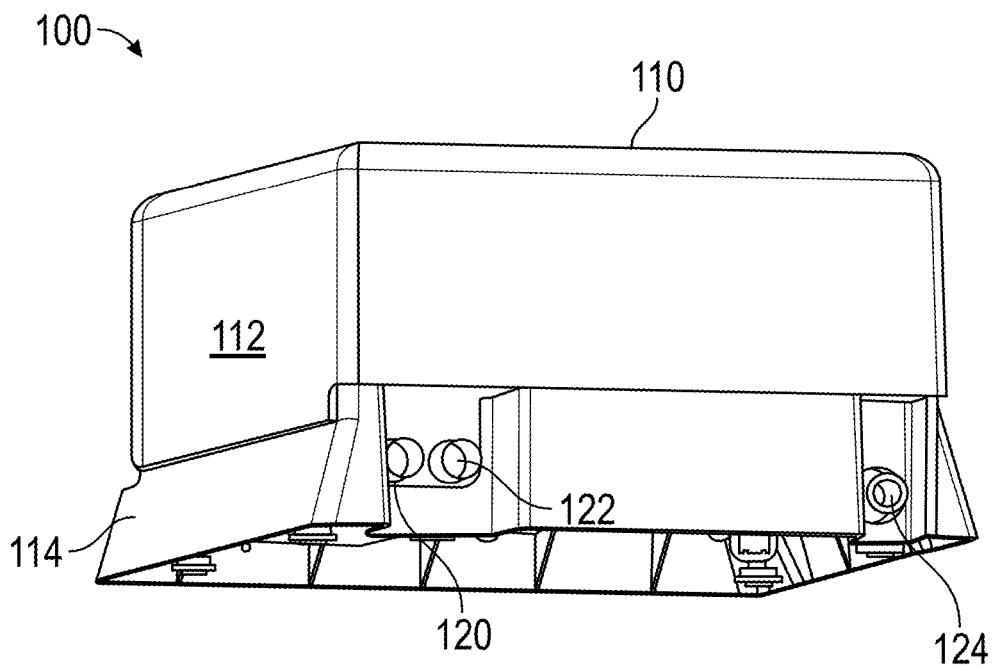
FIG. 3 is a rear perspective view of the CPAP washer of FIG. 2.

Referring now to FIG. 3, the back side of the undermount washer 100 is shown and has a hot water inlet 120, a cold water inlet 122, and a drain outlet 124. The hot water inlet 120 and cold water inlet 122 are to be coupled to the hot water line and the cold water line, respectively, of the sink 14 using a T coupler or other junction to provide hot water and cold water to the undermount washer 100. Likewise, the drain outlet 124 is to be coupled to the drain line of the sink 14 for fluid communication therewith.

Figure 4:
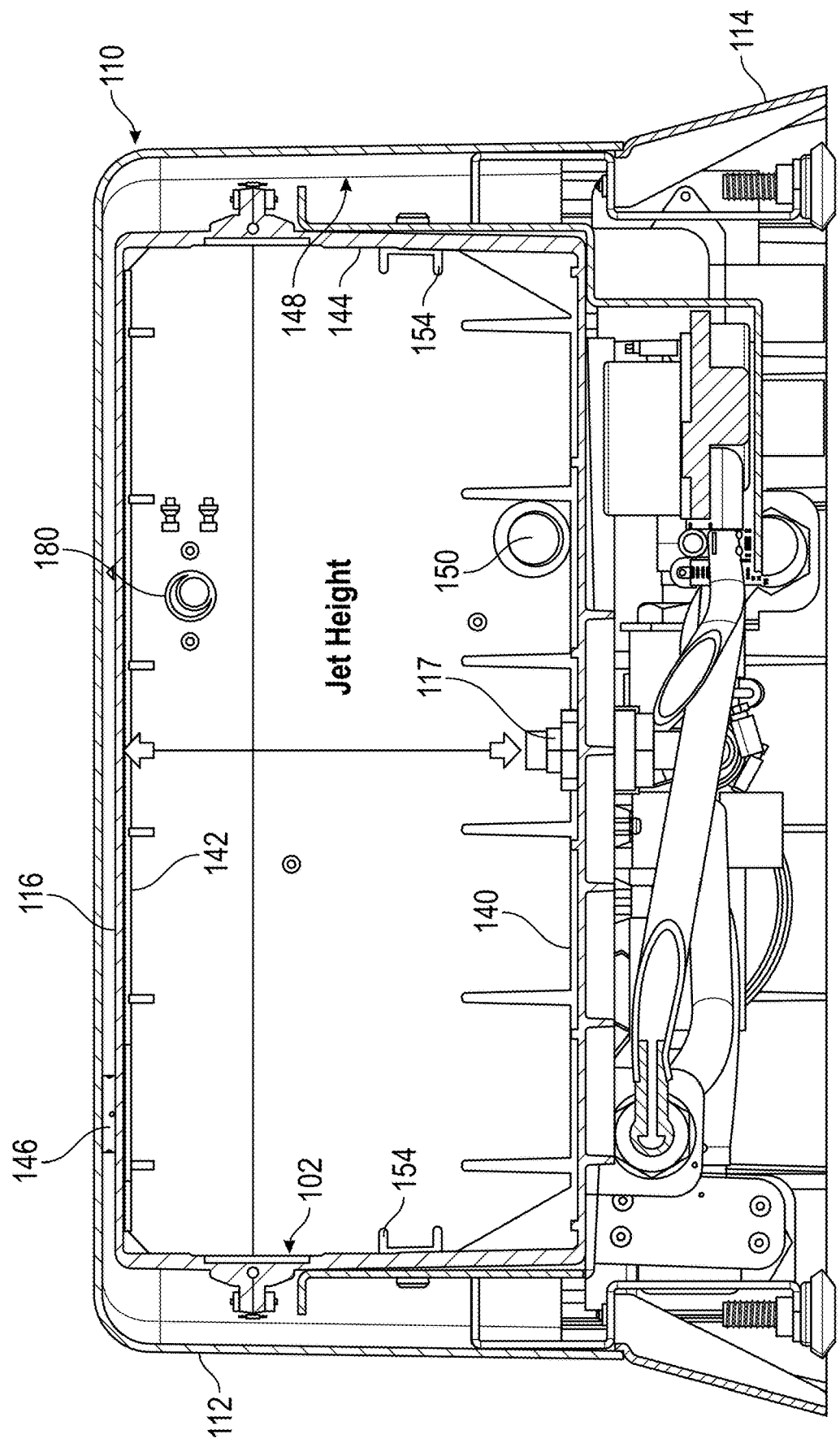
FIG. 4 is a cross-sectional view of the CPAP washer along line 4-4 in FIG. 2
Figure 11:
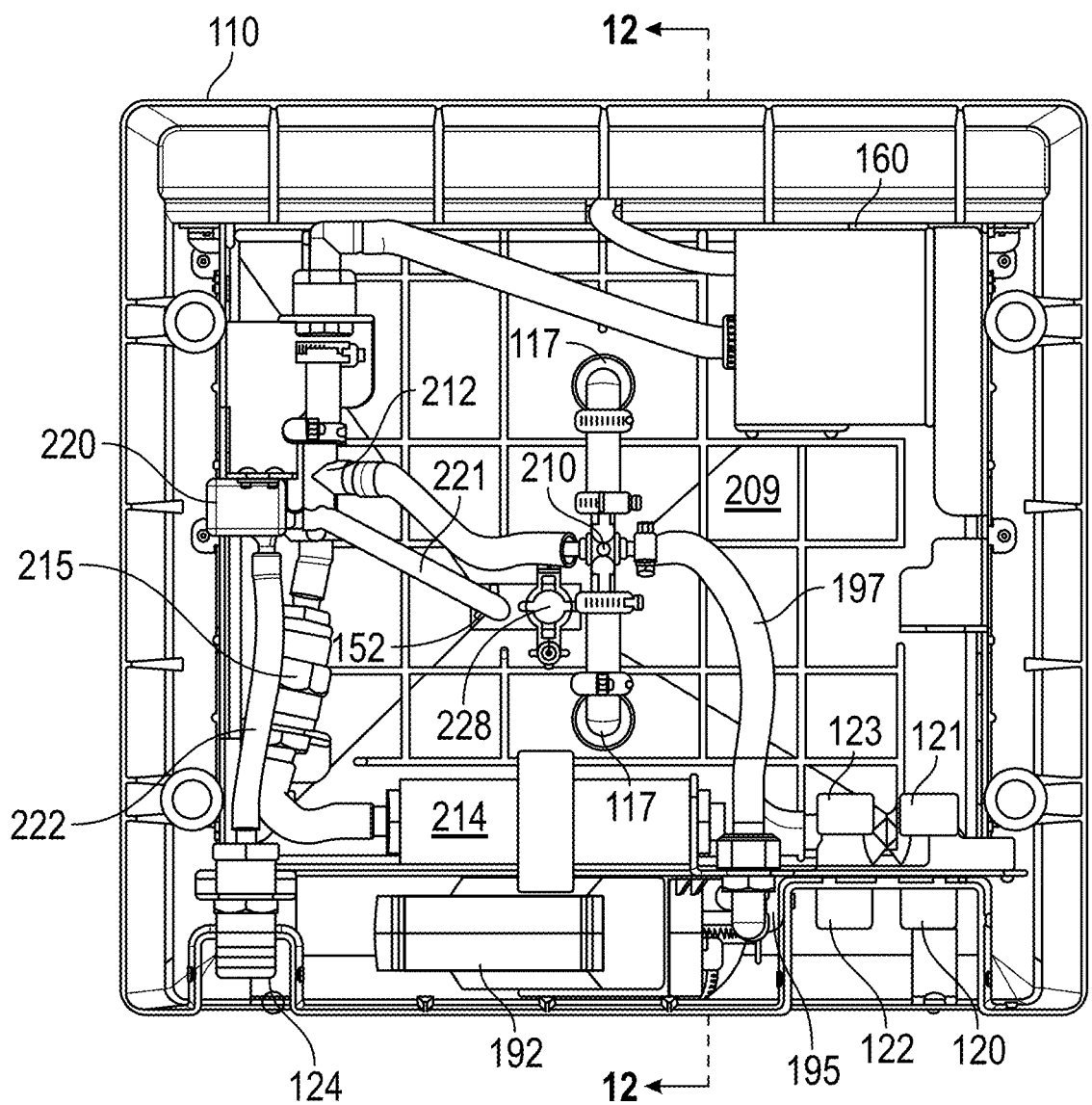
FIG. 11 is bottom view of the CPAP washer of FIG. 2.
Figure 12:
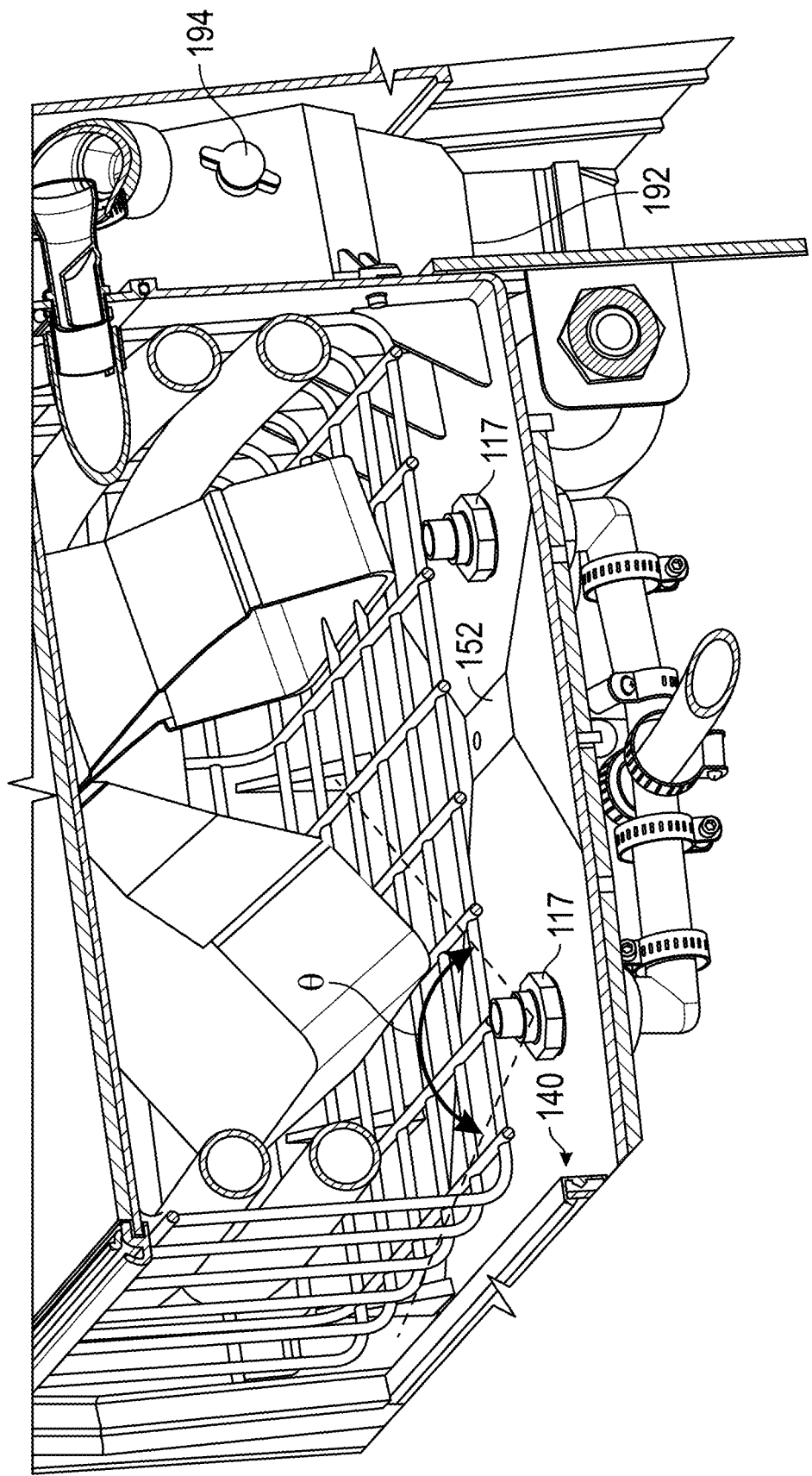
FIG. 12 is a longitudinal cross-section along the plane 12-12 in FIG. 11.

Referring now to FIG. 4, the housing 110, more specifically the inner shell 116 defines the wash chamber 102, which has a bottom surface 140, a top surface 142, and one or more sides 144 extending therebetween. The wash chamber 102 also has an open face 106 (shown in FIG. 1) providing access to the wash chamber 102. A vent port 146 is present in the top surface 142 of the wash chamber 102 and defines a through bore in fluid communication with a void 148 defined between the inner shell 116 and the outer shell 112. This cross-sectional view of the undermount washer 100 reveals a float switch 150 protruding into the wash chamber 102 from the one or more sides 144 proximate the bottom surface 140 and a spray nozzle 117 protruding into the wash chamber 102 through the bottom surface 140. The float switch 150 is present to shut off the introduction of wash water or rinse water into the wash chamber 102 if the drain 152, shown in FIGS. 11 and 12, is not effectively draining water from the wash chamber 102 as wash water or rinse water is introduced therein. The wash chamber 102 also includes wheel-receiving rails 154 mounted therein, typically to opposing sides of the one or more sides 144 of the wash chamber 102, to receive the wheels 172 on the rack 108.

Figure 5:
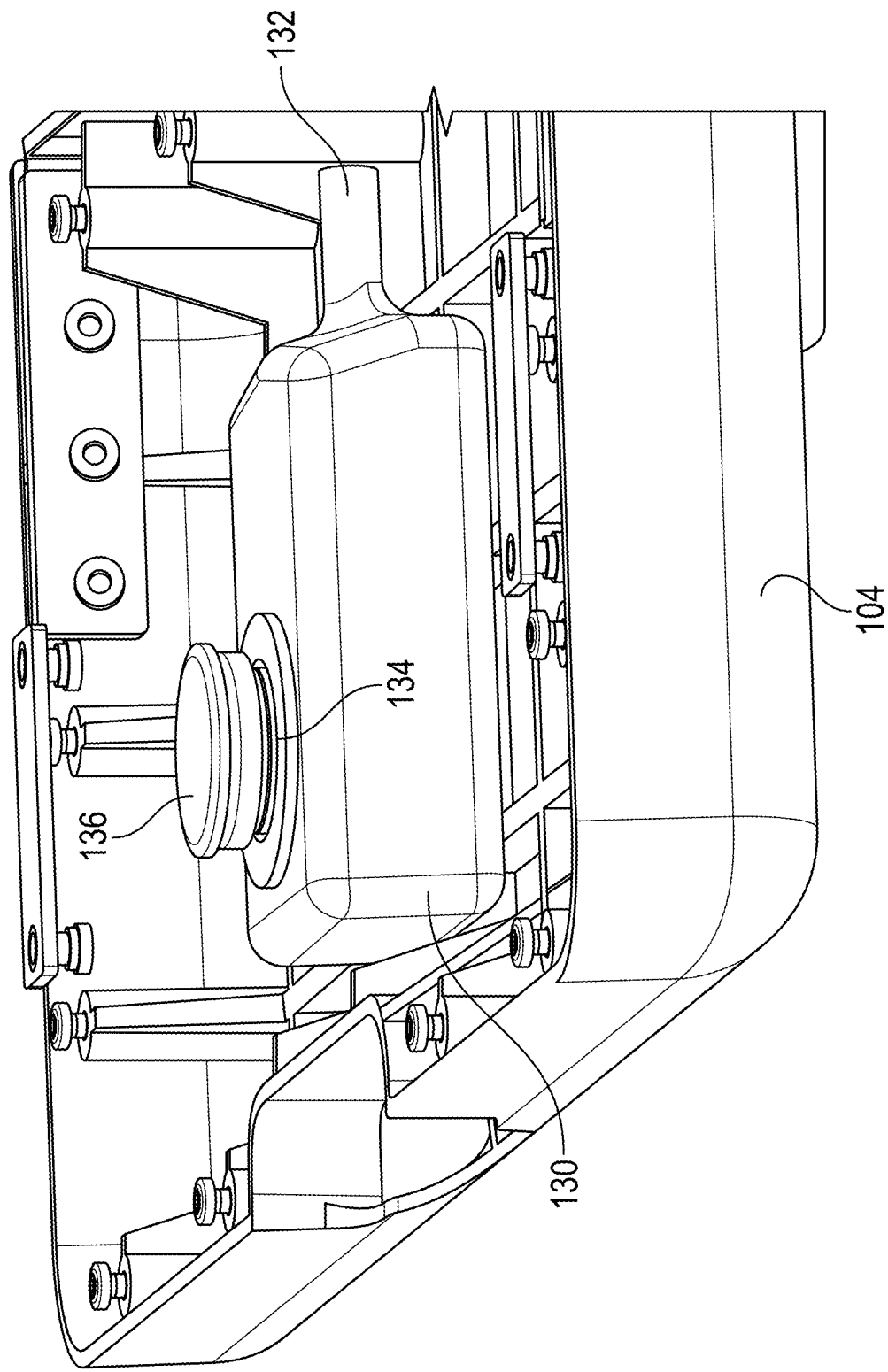
FIG. 5 is a perspective side view of the interior of the door of the CPAP washer of FIG. 2.

Referring now to FIG. 5, the interior of the door 104 is shown and houses a cleaning solution reservoir 130 having an outlet port 132 that is in fluid communication with a dosing pump 160 (shown in FIG. 11) for distribution of the cleaning solution into water within the undermount washer 100. The cleaning solution reservoir 130 has an inlet port 134 for filling and refilling the cleaning solution reservoir 130 which is closable by a releasably attachable cap 136. The inlet port 134 protrudes through a door panel 138 (shown in FIG. 1) to make the cap 136 accessible to the user.

Figure 6A:
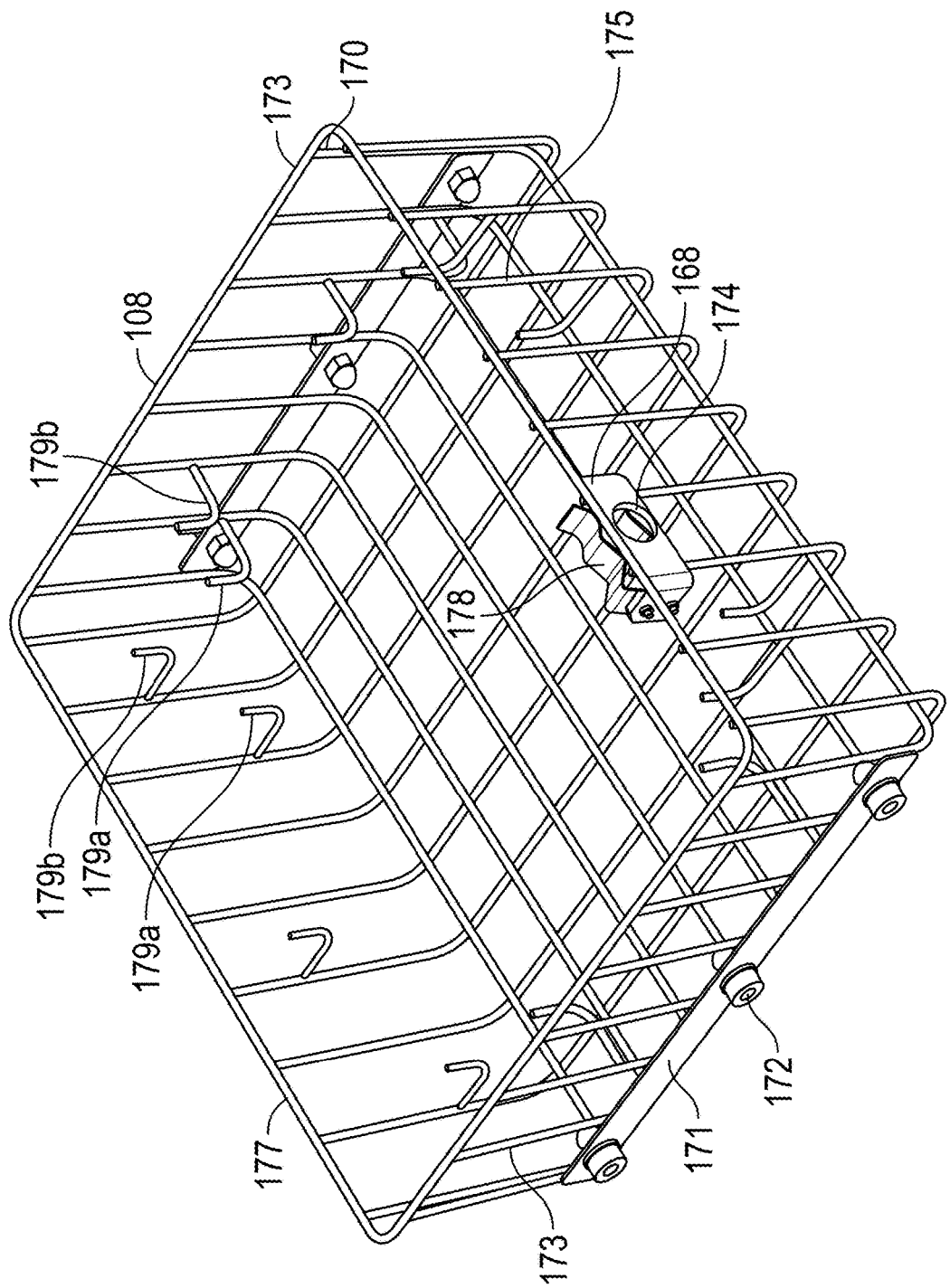
FIG. 6A is a rear perspective view of a rack for the CPAP washer.

Referring now to FIG. 6A, the rack 108 is shown in an enlarged view. The rack 108 is a basket-style rack having a grid-fashioned body 170 to enable the retention of the CPAP equipment to be cleaned while allowing a maximum amount of wash water and/or rinse water through the rack for access to the CPAP equipment. A rail 171 having wheels 172 mounted thereto is mounted to each of opposing sides 173 of the rack 108. The wheels 172 mate with the wheel-receiving rails 154 (FIG. 4) within the wash chamber 102 to facilitate the slidingly receivable nature of rack 108 into the wash chamber 102.

Figure 6B:
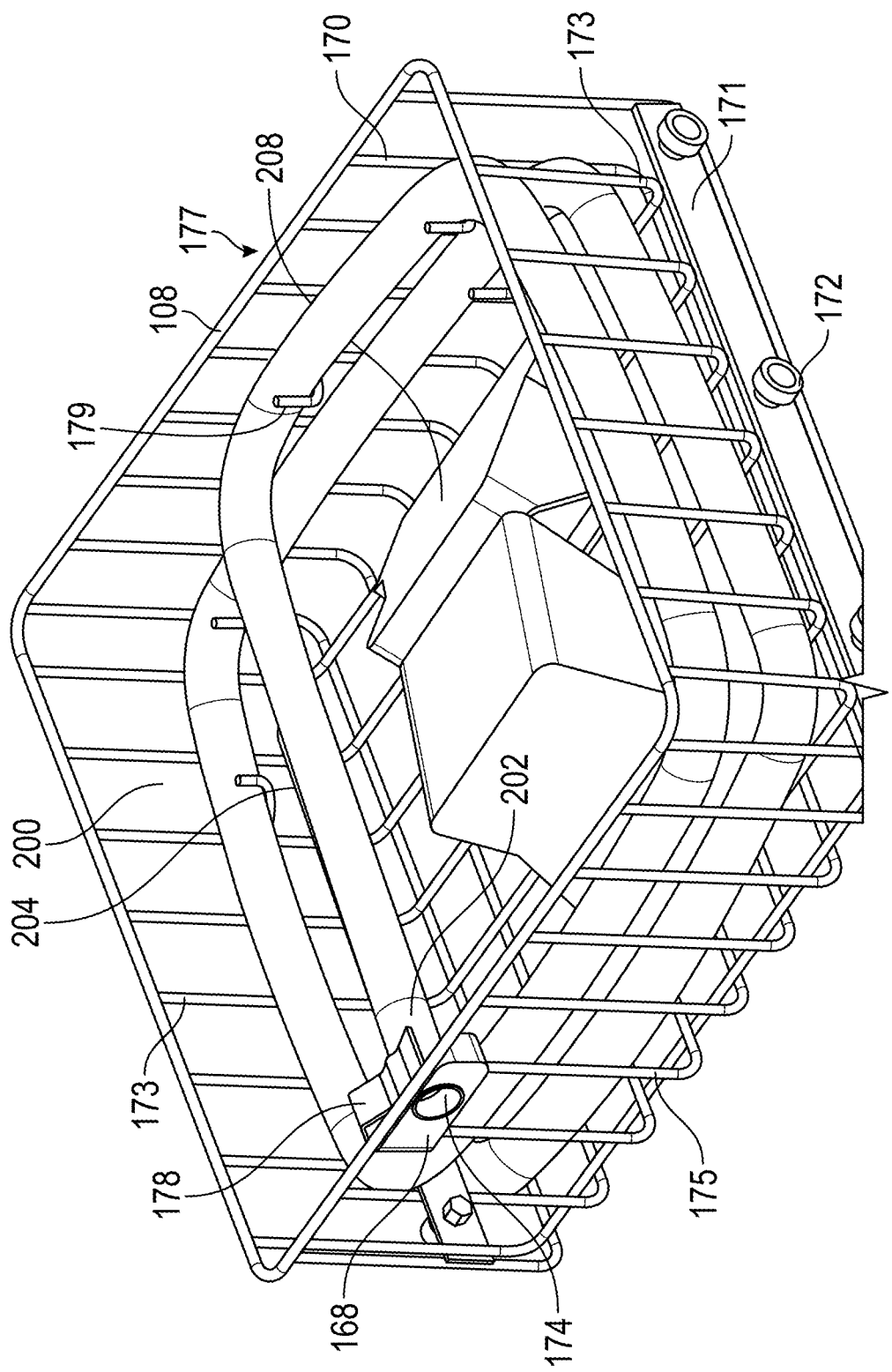
FIG. 6B is a perspective side view of the rack with a CPAP hose and mask therein.
Figure 7:
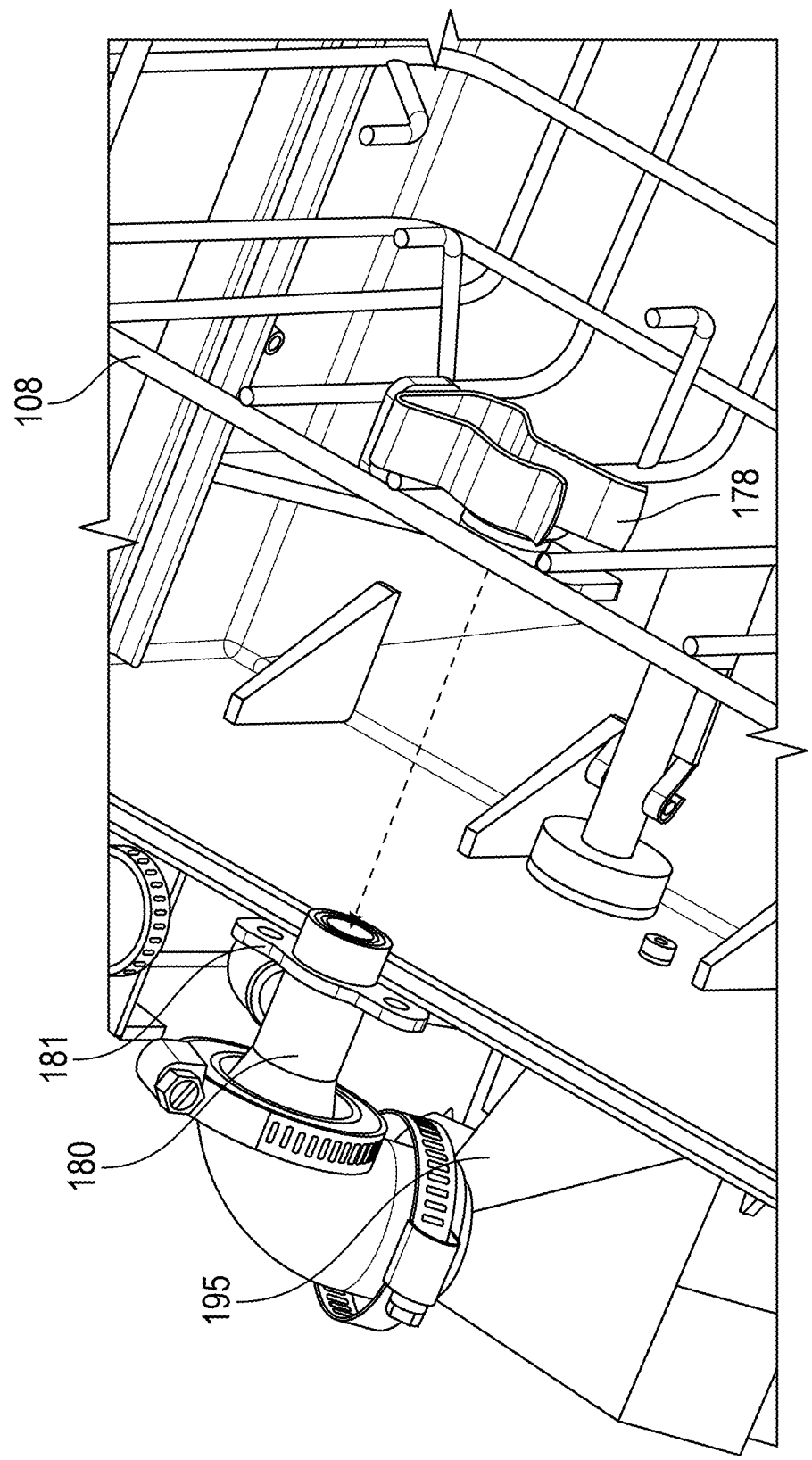
FIG. 7 is an enlarged, partial view of the portion of the rack having the hose connector, which is partially inserted into the wash cavity toward the dual eccentric nozzle of the automatic CPAP washer.
Figure 8:
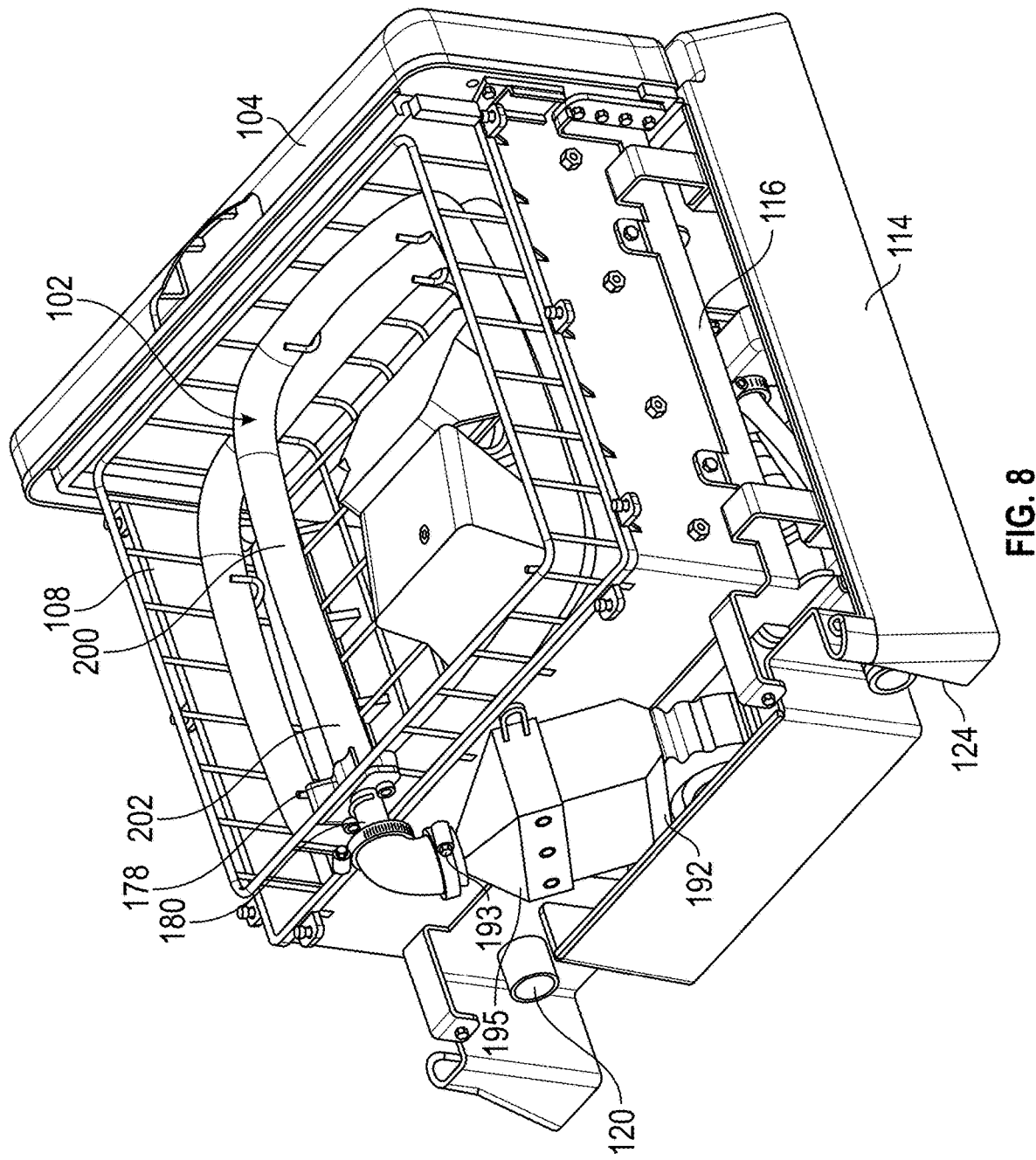
FIG. 8 is a rear-side perspective view of the CPAP washer of FIG. 2 with the rack in the washer chamber and the outer upper portion of the housing removed.
Figure 9:
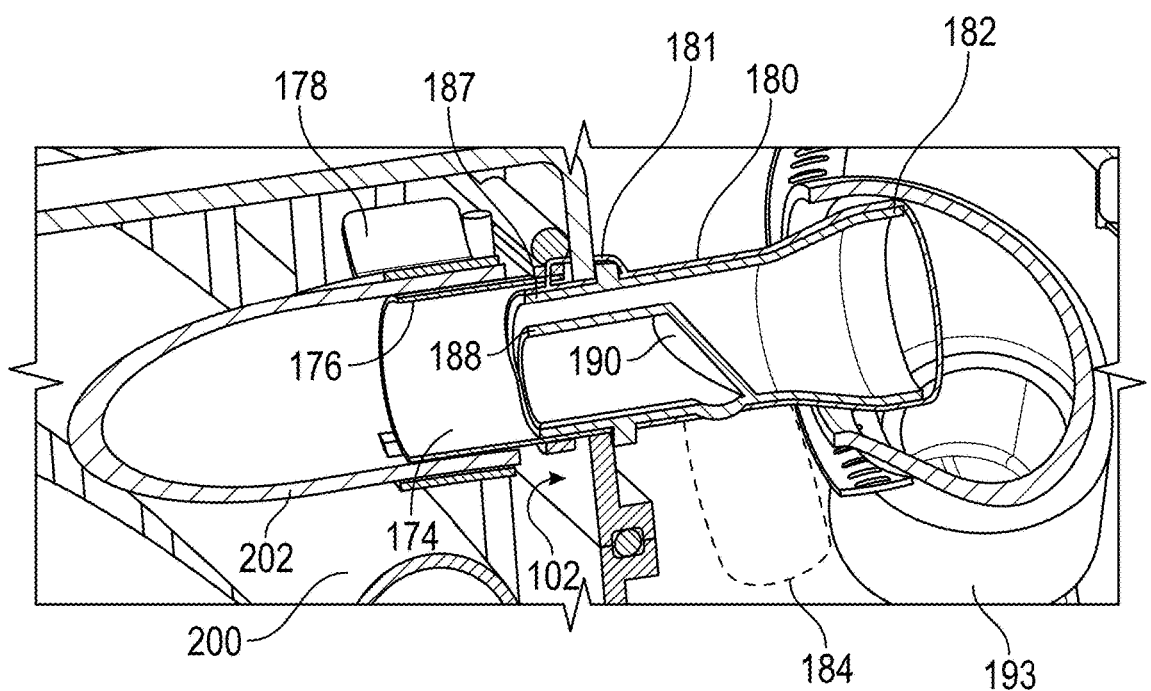
FIG. 9 is an enlarged cut-away view of a dual eccentric nozzle connected to a CPAP hose and an air supply conduit.

Referring now to FIGS. 6-8, in one embodiment, the rack 108 includes a connector tube 174 fixedly connected to the back 175 of the rack 108. The connector tube 174 is fixedly connected to or is integral with the back 175 of the rack. This connection can be facilitated by a generally L-shaped bracket 168. The connector tube 174 protrudes into the void defined by the rack 108 far enough to be inserted into a first end 202 of a CPAP hose 200 when seated in the hose clamp 178. The connector tube 174 preferably defines a male end 176, best seen in the cut-away view of FIG. 9. The hose clamp 178 is oriented to secure an end of the CPAP hose when seated therein with an open end of the hose facing the outlet end 186 of the dual eccentric nozzle 180. The hose clamp 178 releasably attaches the first end 202 of the CPAP hose 200 to the rack 108. Here, the hose clamp 178 can be fixedly connected to the generally L-shaped bracket 168 with the hose clamp 178 oriented parallel to the back 175 of the rack.

Figure 14:
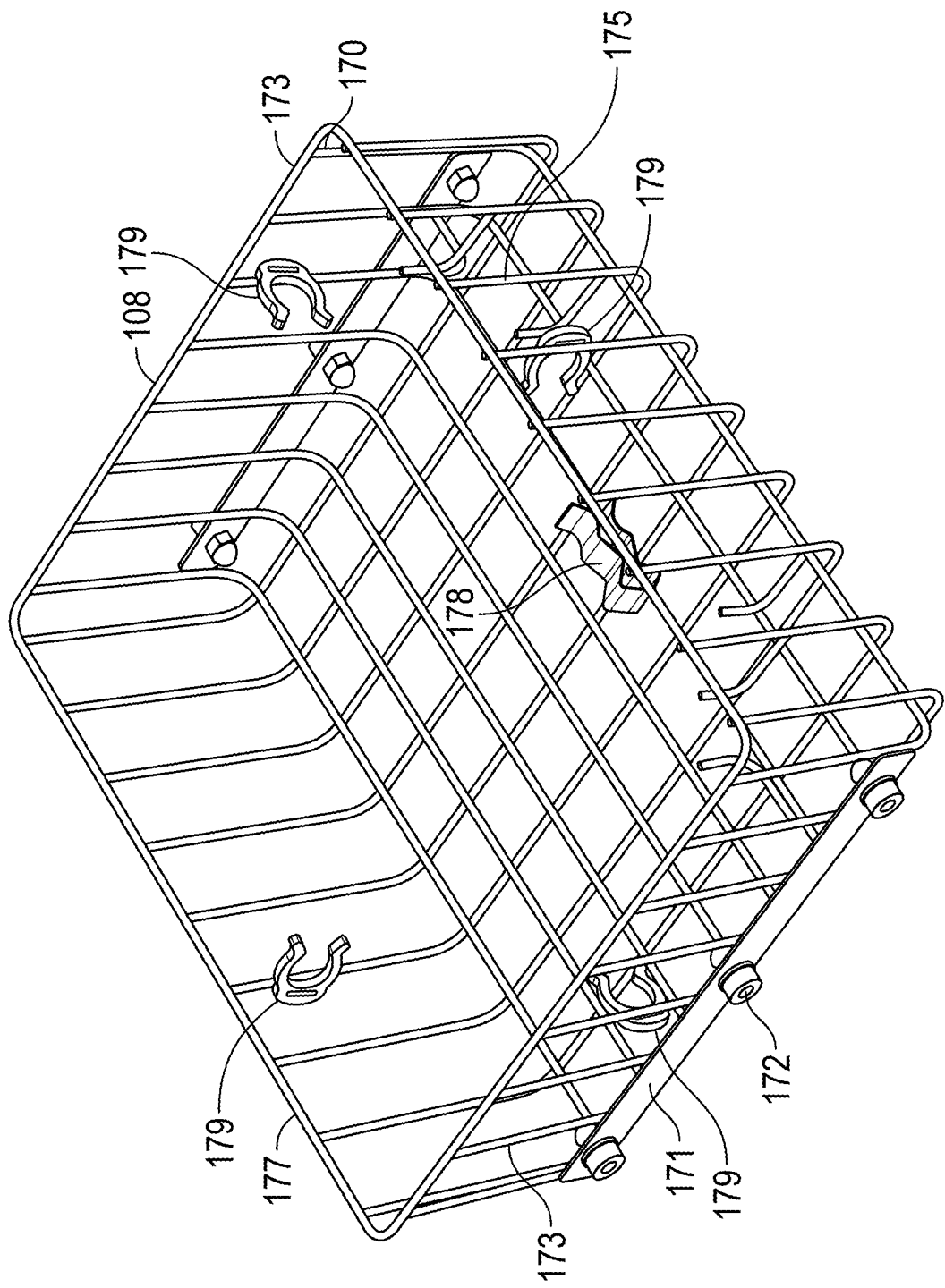
FIG. 14 is a rear perspective view of a rack for the CPAP washer showing an alternative embodiment for the hose routing feature.

Referring now to FIG. 14, in another embodiment, the rack 108 has a hose clamp 178' oriented to secure an end of the CPAP hose 200 when seated therein with an open end 202 facing the outlet end 186 of the dual eccentric nozzle 180, but the outlet end 186 of the dual eccentric nozzle has a length sufficient to be received inside the open end 202 of the CPAP hose 200, without the need for the intermediate tubing 174 shown in the embodiment of FIGS. 6-8. The hose clamp 178' releasably attaches the first end 202 of the CPAP hose to the rack 108.

The hose clamps 178 and 178' shown in the figures is a kick plate spring clamp, but other clamps having a resilient spring action to hold the CPAP hose in place can be used. Another example hose clamp is shown in FIG. 14 for the hose routing feature 179', but is also suitable for the hose clamp 178'. This hose clamp is a flexible plastic C-shaped clip. Any other commercially available or hereinafter developed hose clamps that releasably attach an end of a hose can be used herein.

Referring again to FIGS. 6-8, the rack 108 seats the CPAP hose 200 about interior sides of the opposing sides 173, the back 175 and the front 177 on a plurality of hose routing features 179, such as, but not limited to, the J-shaped hooks illustrated in FIGS. 6A and 6B. As best seen in FIG. 6A, the J-shaped hooks 179 of the interior surfaces of one of the sides 173, the front 177, and the back 175 have a pair of lower hose hooks 179a and upper hose hooks 179b. The lower hooks 179a are offset either to the left or to the right of the upper hooks 179b. The other of the sides 173, may have fewer hooks, because the CPAP hose turns and is connected to the hose clamp 178 before traveling along this side again. The J-shaped hooks 179 may begin at a highest position at the front 177 of the rack or one of the sides 173 and gradually progress lower within the rack moving clockwise or counterclockwise around the interior of the rack, depending upon which way the CPAP hose is intended to be coiled within the rack.

Referring now to FIG. 14, rack 108 is shown to have an alternate embodiment for the hose routing feature, here reference 179'. In this embodiment, the hose routing feature 179' is a C-shaped clamp protruding into the cavity defined by the rack 108 or a combination of C-Shaped clamps 179' and J-shaped hooks 179. The C-shaped clamp has a spring resilient feature such that the opposing arms of the C-shape are expandable when a hose is inserted and returnable to an original position to hold the hose securely therein during operation of the cleaning device. Other hose clamps styles to which the hose is releasably attachable include a tubing clamp available from HACH® of Loveland, Colorado. Additionally, a hook-and-loop material strap connectable to itself could hold the hose instead of the C-shaped clamps or the rack could include one or more strategically placed pieces of either the hook material or the loop material fixedly attached to the rack and the hose of the CPAP machine could include the opposite of said material for matingly receiving the hose to the rack. Any combination of the possible hose routing features can be present in the rack 108. In all embodiments, the hose routing features begin at a highest position at the front 177 of the rack or one of the sides 173 and gradually progress lower within the rack moving clockwise or counterclockwise around the interior of the rack, depending upon which way the CPAP hose is intended to be coiled within the rack.

As shown in FIG. 6B, the second end 204 of the CPAP hose 200 lies in the rack 108 in an unconnected, unobstructed manner, thereby enabling wash water or rinse water running through the CPAP hose to flow into the wash chamber 102 and to the drain 152. The rack 108 is sized to hold a CPAP mask, shown in FIG. 1, and a CPAP humidifier water chamber 208 interiorly relative to the coils of the CPAP hose 200.

Figure 10:
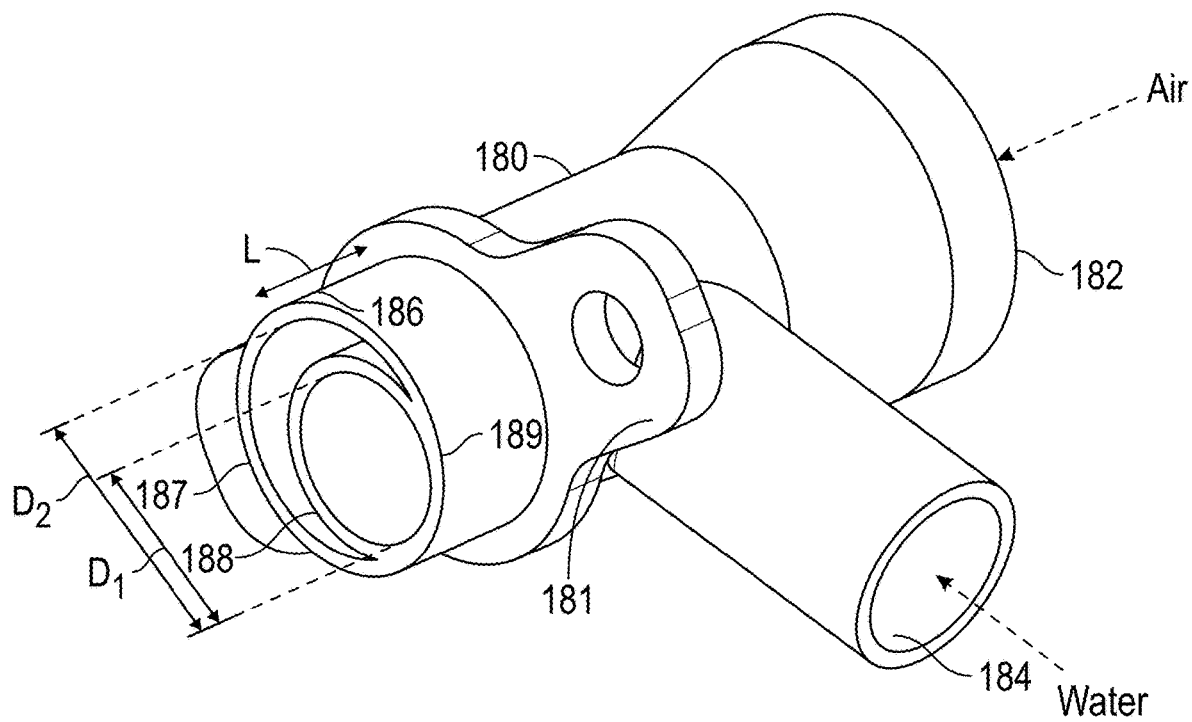
FIG. 10 is an end perspective view of the dual eccentric nozzle.
Figure 15A:
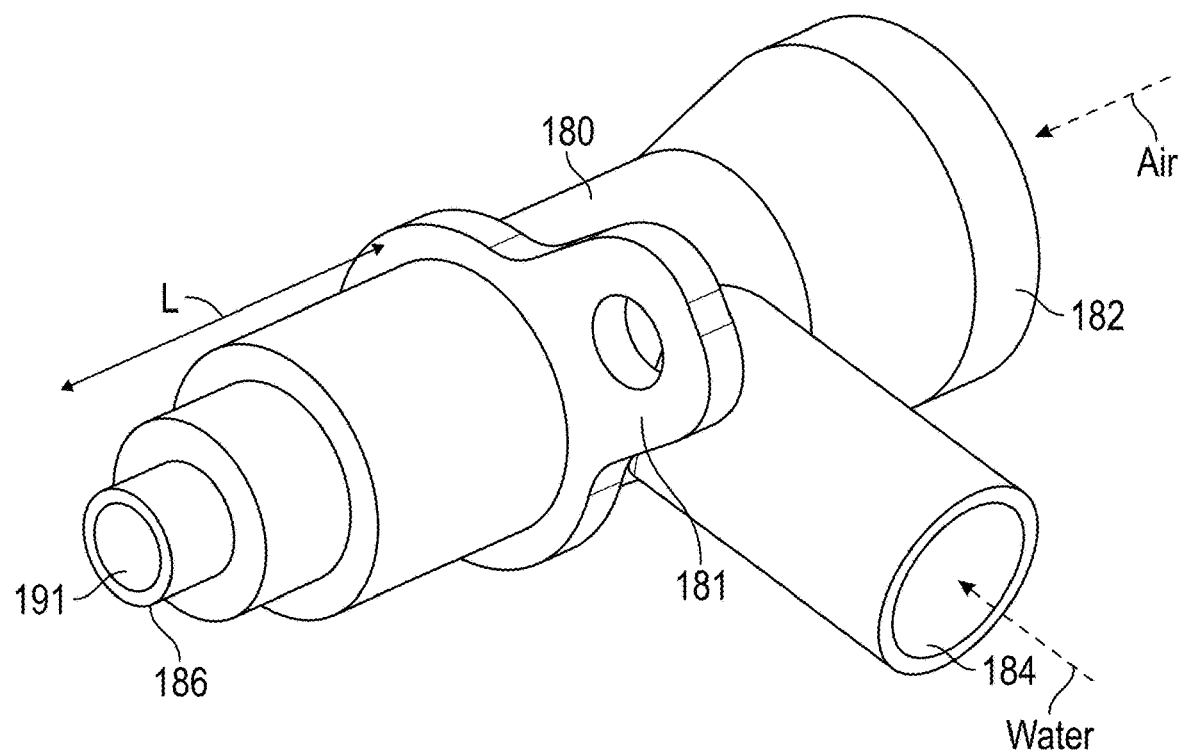
FIG. 15A is a second embodiment of the dual eccentric nozzle.
Figure 15B:
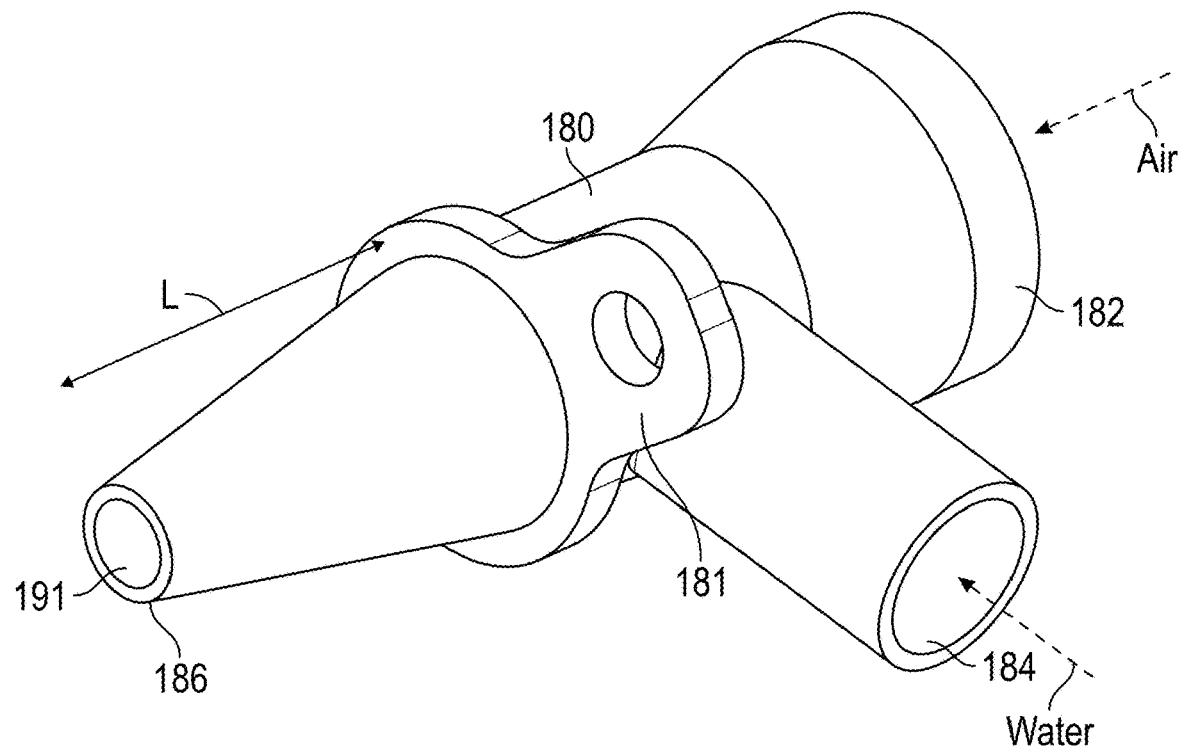
FIG. 15B is a third embodiment of the dual eccentric nozzle.

Referring now to FIGS. 7-10, a dual eccentric nozzle 180 protrudes into the wash chamber 102 at a position aligned to mate with the connector tube 178 of the rack 108 when the rack is fully seated within the wash chamber 102, i.e., has reached its limit of travel inside the wash chamber. A mounting flange 181 extends outward from the body of the dual eccentric nozzle 180 and seats flush against a side wall 144 of the wash chamber 102 to secure (releasably or fixedly) the dual eccentric nozzle 180 thereagainst. The end of the dual eccentric nozzle 180 positioned within the wash chamber 102 is shown as a male end 181 seated within the connector tube 174, in FIG. 9, but the opposite configuration is also possible. As shown in FIG. 10, the outlet end 186 has a cylindrical tube shape for its exterior surface. In the alternate embodiments shown in FIGS. 15A and 15B, the exterior surface of the outlet end 186 can have a stepped conical shape (FIG. 15A) that narrows toward the outlet opening 191 or a smooth, gradually tapering conical shape (FIG. 15B) that narrows toward the outlet opening 191. In all embodiments, the length (L) of the outlet end 186 is in a range of about 0.5 in to 2 inches.

The dual eccentric nozzle 180 fluidly connects the connector tube 178 to both air and water. More specifically, an air input conduit 182 of the dual eccentric nozzle 180 introduces air into the CPAP hose 200 during a drying cycle and a water inlet conduit 184 of the dual eccentric nozzle 180 introduces water into the CPAP hose 200 during a rinse cycle without mixing of the air and the water.

As best seen in FIG. 10, the outlet end 186 of the dual eccentric nozzle 180 defines eccentric conduits having an outer tube 187 and an inner tube 188 that are integral with one another, the outer tube 187 defining the exterior surface of the outlet end 186 and being spaced apart from the inner tube 188 except where the outer and inner tubes 187, 188 share a common arc 189. The space between the outer tube 187 and the inner tube 188 defines the a pathway for air flow, and, as shown in the cross-section of FIG. 9, the outer tube 187 has a divider 190 fluidly separating the air inlet conduit 182 from the water inlet conduit 184 so that the air and water do not mix. As expected by the names, inner tube and outer tube, the inner tube 188 has a diameter $D_1$ that is smaller than the diameter $D_2$ of the outer tube 187. $D_2$ may be about 5 mm larger or about 4 mm larger than $D_1$. The water inlet conduit 184 and the air inlet conduit 182 may form a 80 degree angle as shown, but is not limited thereto.

Referring again to FIGS. 7-9 and to FIG. 11-12, a heated blower unit 192 is in fluid communication with the air inlet conduit 182 of the dual eccentric nozzle 180. The heated blower unit 192 and the air inlet conduit 182 are connected by tubing 193, which can be flexible tubing, by releasably attachable fasteners that form airtight seals/connections. The heated blower unit 192 heats air to a maximum temperature of 110° F. (43.3° C.) and has a temperature switch 194, visible in FIG. 12, that turns off the blower if the air temperature reaches 111° F. (43.9° C.). And, the water inlet conduit 184 is in fluid communication with wash water or rinse water flowing from a splitter coupler 210, shown in FIG. 11, in fluid communication with sprayer nozzles 117, all of which are in fluid communication with a mixing T coupler 212. Flexible tubing 195 leads from the water inlet conduit 184 and extends to the other fluid components located along a bottom exterior surface 209 of the housing 110, which includes a fluid tight connection to flexible tubing 197 that connects directly to the splitter coupler 210.

Referring to FIG. 11, the hot water inlet 120 is controlled by an electrically actuated valve 121 and a cold water inlet 122 is optionally controlled by an electrically actuated valve 123. The electrically actuated valves 122 and 123 are in communication with a controller that is in electrical communication with a temperature sensor or temperature switch 228. The controller is set to open the electrically actuated valve 121 to introduce hot water when the temperature is below 59° F. and is set to close the electrically actuated valve 121 to stop the introduction of hot water when the temperature of the mixed water rises to about 90° F. or about 100° F. The temperature switch 228 is configured to shut off the flow of hot water so that the mixed water temperature does not reach or exceed 111° F. For example, the temperature switch may be a bimetallic disc thermostat having a preselected "open on rise" or "close on rise" temperature range suitable to control the temperature of the wash water and rinse water in the range set forth below.

The hot water inlet 120 and the cold water inlet 122 are in fluid communication with one another to mix the hot and cold water to form mixed water having a temperature within the range of 60° F. to 100° F. (15.6° C. to 37.8° C.). The mixed water is in fluid communication with a pressure regulator 214 to reduce the water pressure to be in a range of 5 psi to 50 psi (34.5 kPa to 344.7 kPa). The pressure regulator 214 is in fluid communication with a flow restrictor 215 to reduce the flowrate of the mixed water. The mixed water after flowing through the pressure regulator 214 and then the flow restrictor 215 has a psi in the range noted above and a flow rate in gallons per minute of less than 2 gpm, more preferably less than 1 gpm. In one embodiment, the flow rate is between 0.5 gpm to 0.75 gpm at the introduction of mixed water into the mixing T coupler 212 and into the wash chamber 102. The reduced pressure water is in fluid communication with the mixing T coupler 212, and the mixing T coupler 212 is in fluid communication with a dosing pump 160 for mixing cleaning solution from the cleaning solution reservoir 130 with the reduced pressure water in the mixing T coupler 212, thereby forming wash water that is distributed to the splitter coupler 210 for distribution to the spray nozzles 117 and to the dual eccentric nozzle 180 for introduction into the wash chamber 102 and the CPAP hose 200, respectively, thereby washing or rinsing the inside and the outside of CPAP hose simultaneously. The splitter coupler 210 is a 4-way coupler, but is not limited thereto. The splitter coupler is dependent upon the number of spray nozzles 117 selected to be present in the undermount washer. The splitter is a 4-way coupler in FIG. 11 because two spray nozzles 117 are shown.

Referring now to FIG. 12, one or more spray nozzles 117 protrude through the bottom surface 140 of the wash chamber 102 with a fluid tight seal therebetween. Each spray nozzle 117 is a cone-shaped spray nozzle, preferably with a 120 degree spray cone θ, and jets the spray to the top surface 116 of the wash chamber 102 as represented by the arrow labeled "jet height" in FIG. 4.

Returning to FIG. 11, the fluid components include a drain pump 220 in fluid communication with the drain 152 in the bottom surface 140 of the wash chamber 102, which may be accomplished by flexible tubing 221, and in fluid communication with drain outlet 124, which may be accomplished by flexible tubing 222. In operation, the drain pump 220 is active simultaneously with the introduction of rinse water or wash water so that the CPAP equipment always experiences a continuous flow from the water source rather than internally recycled water. Any reference to flexible tubing herein may instead be rigid conduit tubing, if desired, and all connections are to be fluid tight connections whether permanently fixed connections or releasably attachable connections. Releasably attachable connections may be preferred for future replacement of parts.

Referring back to FIG. 1, the undermount washer 100 includes a magnetic switch 107 in the frame of the outer shell 112 that defines the open face 106 that will turn off the flow of rinse water or wash water or air if the door 104 is opened by a user while the washer 100 is "on."

The washer 100 can be an undermount model for direct connections to plumbing, typically the plumbing of a sink, but the model is not limited thereto. When connected to a sink, the pipe connected to the base of the sink is replaced with a branched pipe for connection of a drain line in fluid communication with the drain outlet 124 of the washer to the branch of the branched pipe. Then, in each of the hot water line and the cold water line, a tee and a shut off valve are installed for connection to the hot water inlet 120 and cold water inlet 122, respectively, of the washer.

The washer 100 can be a portable model that sits on a countertop and is repeatedly, removably attachable to a faucet and the drain line is placed in an appropriate receptable, such a sink, a floor drain, or a container having sufficient volume to collect wash and drain water. Any commercially available faucet adapter can be used, such as an appliance unicouple available from GE for appliances.

Figure 13:
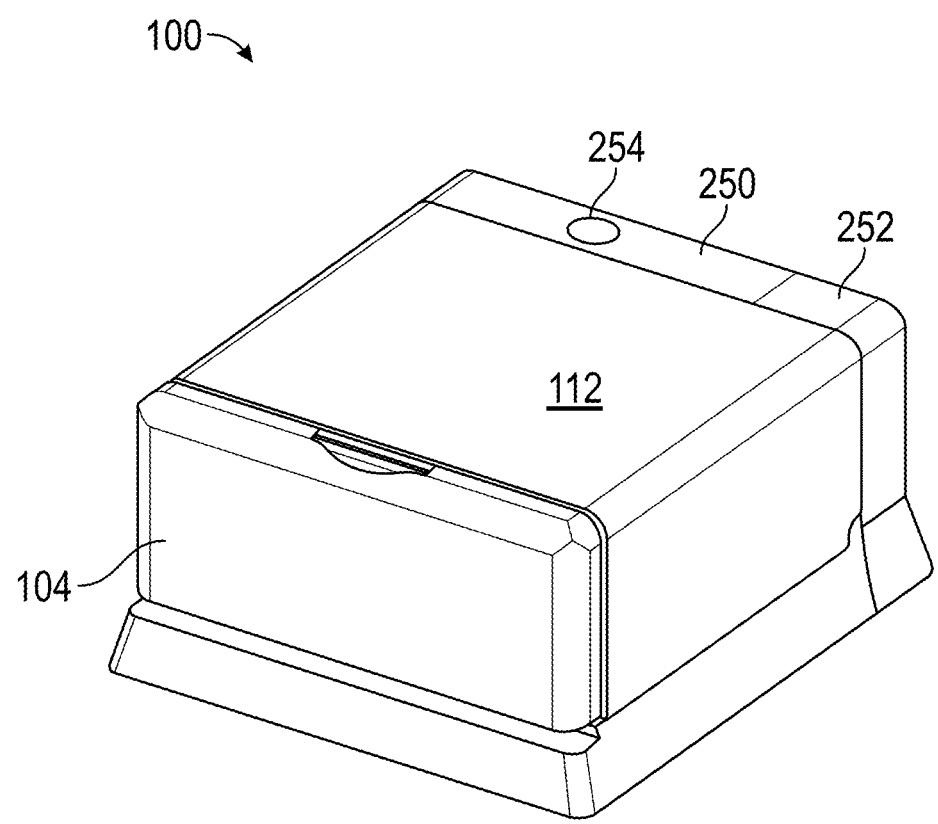
FIG. 13 is a front perspective view of a portable automatic CPAP washer.

Referring now to FIG. 13, in another embodiment, the washer 100' can have an on-board reservoir 250 of sufficient volume to hold wash water and rinse water for the device and a water heater 252 for heating part or all of the water stored in the reservoir. A fill port 254 is in fluid communication with the on-board reservoir. The reservoir 250 can be sized to hold 5 liters of water up to 20 liters of water including any liter increment therebetween. Here, the drain line is placed in an appropriate receptacle, such as a sink, a floor drain, or a container having sufficient volume to collect wash and drain water.

In all aspects, the washer 100 has a footprint that is generally less than 20 in×21 in×23 in. In one embodiment, the footprint is less than 20 in×20 in×10 in. In another embodiment, the footprint is less than 16 in×16 in×10 in. The housing 110 may be made of plastic or stainless steel or a combination thereof.

In operation, the washer 100, whether an undermount model, a portable model, or a self-contained model, has a two-stage cleaning cycle that includes a cold rinsing cycle before a hot rinsing cycle. The cold rinsing cycle begins with cold water introduction for 60 seconds with the continuous draining of the rinse water as described herein. Then, the dosing pump 160 will dispense a first pre-selected amount of cleaning solution to the mixing T coupler 212 and cold water will enter for 120 seconds including mixing with the cleaning solution and introduction as wash water into the wash chamber 102 and into the CPAP hose 200 along with continuous draining of the wash water.

The hot rinsing cycle begins with a flow of hot and cold water for 60 second, which mix to introduce rinse water into the wash chamber 102 and the CPAP hose 200 at a temperature in a range of 60° F. to 100° F., with the continuous draining of the rinse water. Next, the dosing pump 160 will dispense a second pre-selected amount of cleaning solution to the mixing T coupler 212 and cold water will enter for 120 seconds including mixing with the cleaning solution and introduction as wash water into the wash chamber 102 and into the CPAP hose 200 along with continuous draining of the wash water. Lastly, a flow of hot and cold water for 120 seconds, which mix to introduce rinse water into the wash chamber 102 and the CPAP hose 200 at a temperature in a range of 60° F. to 100° F. with continuous draining of the rinse water. The two-stage cleaning cycle may use about 20 L of water.

The first and second pre-selected amount of cleaning solution may be the same or different. When the pre-selected amounts of cleaning solution are different, the second pre-selected amount of cleaning solution is less than the first pre-selected amount of cleaning solution. The cleaning solution is preferably a mild, gentle soap that is free of perfumes. Some liquid cleaning solutions that are suitable include, but are not limited to, Dr. Bonner's unscented liquid soap, IVORY® or DAWN® dishwashing detergent, and JOHNSON'S® baby shampoo.

Subsequent to the two-stage cleaning cycle, a drying cycle is executed. Here, the heated blower unit 192 introduces air having a temperature not to exceed 110° F., for a pre-determined period of time. The pre-selected drying time is in a range of 5 minutes to 30 minutes, more preferably 15 minutes to 30 minutes. The heated air is first introduced into the CPAP hose 200, and after exiting the CPAP hose, the heated air circulates inside the wash chamber 102 before exiting the wash chamber 102 through the vent 146, which releases the heated air to the atmosphere. This will dry all the parts inside the wash chamber 102.

The undermount washer has many advantages including, but not limited to, providing a user friendly washer for CPAP equipment that can be undermount under a kitchen or bathroom sink for direct connection to the hot and cold water lines leading to the sink and to the drain leading from the sink. The undermount washer uses a mix of hot and cold water during wash and/or rinse cycles to achieve a safe temperature for CPAP equipment without using a heater unit. This greatly reduces the risk of over-heating the water and/or the washer itself. The undermount washer uses a continuous flow of fresh wash water and fresh rinse water that drains immediately from the wash chamber, i.e., no internally recycled water is reintroduced to the interior or the exterior of the CPAP hose or other CPAP equipment, thereby providing a better clean than prior devices. And, the undermount washer uses cleaning solution and water for a safe and effective cleansing of the CPAP equipment rather than ozone or UV light.

It should be noted that the embodiments are not limited in their application or use to the details of construction and arrangement of parts and steps illustrated in the drawings and description. Features of the illustrative embodiments, constructions, and variants may be implemented or incorporated in other embodiments, constructions, variants, and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

Having described the invention in detail and by reference to preferred embodiments thereof, it will be apparent that modifications and variations are possible without departing from the scope of the invention which is defined in the appended claims.

What is claimed is:

1. A washer for continuous positive airway pressure (CPAP) equipment comprising:
    a housing defining a wash chamber and defining an opening providing access to the wash chamber;
    a door selectively closing the opening;
    a first nozzle protruding into the wash chamber; and
    a rack receivable within the wash chamber, the rack comprising a connector tube configured to orient and secure an end of a CPAP hose when seated in the rack with an open end of the CPAP hose facing the nozzle;
    wherein the first nozzle has an air conduit that introduces air during a drying cycle and a water conduit that introduces water during a rinse cycle;
    wherein, in a fully inserted position of the rack in the wash chamber, the first nozzle is mated to the connector tube, thereby providing fluid flow inside the CPAP hose when present.

2. The washer as claimed in claim 1, further comprising a second nozzle configured to spray water into the wash chamber.

3. The washer of claim 2, wherein the second nozzle protrudes into the wash chamber and is a cone-shaped spray nozzle.

4. The washer as claimed in claim 2, wherein the second nozzle has a 120 degree spray cone.

5. The washer as claimed in claim 2, comprising a hot water inlet controlled by an electrically actuated valve and a cold water inlet, wherein the cold water inlet and the hot water inlet are in fluid communication with one another to mix the hot and cold water to form mixed water having a temperature within the range of 60° F. to 100° F. (15.6° C. to 37.8° C.).

6. The washer as claimed in claim 5, wherein the mixed water is in fluid communication with a pressure restrictor to reduce the water pressure to be in a range of 5 psi to 50 psi (34.5 kPa to 344.7 kPa) at introduction to the wash chamber, thereby forming reduced pressure water.

7. The washer as claimed in claim 6, wherein the reduced pressure water is in fluid communication with a mixing T coupler and the mixing T coupler is in fluid communication with a dosing pump for mixing cleaning solution with the reduced pressure water in the mixing T coupler, thereby forming wash water.

8. The washer as claimed in claim 7, comprising a cleaning solution reservoir in fluid communication with the dosing pump.

9. The washer as claimed in claim 7, wherein the mixing T coupler is in fluid communication with the second nozzle and the water conduit of the first nozzle to introduce wash water inside the CPAP hose and to the outside of the CPAP hose simultaneously.

10. The washer as claimed in claim 1, further comprising a plurality of spray nozzles protruding from one or more surfaces of the wash chamber.

11. The washer as claimed in claim 1, comprising a heated blower unit in fluid communication with the air conduit of the first nozzle.

12. The washer as claimed in claim 11, wherein the heated blower unit heats air to a maximum temperature of 110° F. (43.3° C.).

13. The washer as claimed in claim 1, wherein the rack has a plurality of hose routing features about interior sides of the rack.

14. The washer as claimed in claim 1, comprising a drain pump in fluid communication with a drain in a bottom surface of the wash chamber, wherein the drain pump is active simultaneously with the introduction of water or wash water into the wash chamber.

15. The washer as claimed in claim 1, comprising an on-off switch and a start-stop switch.

16. The washer as claimed in claim 1, comprising a water reservoir in controlled fluid communication with the first nozzle.

17. The washer as claimed in claim 16, wherein the water reservoir is a portion of the housing.

18. The washer as claimed in claim 1, wherein the housing defines a countertop unit or a portable unit.

19. The washer as claimed in claim 1, wherein the housing defines an undermount unit.

20. The washer as claimed in claim 1, wherein the washer has a two-stage cleaning cycle comprising a cold rinsing cycle before a hot rinsing cycle.

\* \* \* \* \*